United States Patent [19]

Kim et al.

[11] Patent Number: 5,470,815
[45] Date of Patent: Nov. 28, 1995

[54] MULTICOMPONENT OXIDE CATALYST

[75] Inventors: Jong-Seob Kim, Taejon; Seong-Ihl Woo, Seoul, both of Rep. of Korea

[73] Assignee: Korea Advanced Istitue of Science and Technology, Rep. of Korea

[21] Appl. No.: 175,286

[22] Filed: Dec. 29, 1993

[30] Foreign Application Priority Data

Dec. 31, 1992 [KR] Rep. of Korea .................. 92-27095

[51] Int. Cl.⁶ .................. B01J 23/10; B01J 23/28
[52] U.S. Cl. .................. 502/304; 502/306; 502/308; 502/317; 502/321; 502/322; 502/323; 502/328; 502/330; 502/332; 502/337; 502/340; 502/341; 502/344; 502/348; 502/349; 502/353; 502/354
[58] Field of Search ............... 502/311, 306, 502/313, 314, 308, 389, 310, 321, 322, 304, 317, 323, 328, 330, 332, 337, 340, 341, 344, 348, 349, 353, 354

[56] References Cited

U.S. PATENT DOCUMENTS

| | | | |
|---|---|---|---|
| 3,118,928 | 1/1964 | Garrison et al. | 260/465.3 |
| 3,125,538 | 3/1964 | Arnold et al. | 252/454 |
| 3,670,006 | 6/1972 | Taylor | 260/465.3 |
| 3,670,008 | 6/1972 | Taylor | 260/465.3 |
| 3,670,009 | 6/1972 | Taylor | 260/465.3 |
| 3,678,090 | 7/1972 | Taylor | 260/465.3 |
| 3,686,267 | 8/1972 | Taylor | 260/465.3 |
| 3,746,737 | 7/1973 | Tullman | 260/465.3 |
| 3,816,506 | 6/1974 | Taylor | 260/465.3 |
| 3,833,638 | 9/1974 | Knox et al. | 260/465.3 |
| 3,860,534 | 1/1975 | Harris et al. | 252/461 |
| 4,000,178 | 12/1976 | Kahney et al. | 260/465.3 |
| 4,036,870 | 7/1977 | Augustus et al. | 260/465.3 |
| 4,052,450 | 10/1977 | Krabetz et al. | 502/310 |
| 4,609,502 | 9/1986 | Khoobiar et al. | 558/320 |
| 4,736,054 | 4/1988 | Attig et al. | 558/319 |
| 4,746,641 | 5/1988 | Guttmann et al. | 502/202 |
| 4,760,159 | 7/1988 | Suresh et al. | 558/319 |
| 4,767,739 | 8/1988 | Glaeser et al. | 502/209 |
| 4,769,355 | 9/1988 | Glaeser et al. | 502/209 |
| 4,783,545 | 11/1988 | Glaeser et al. | 558/319 |
| 4,784,979 | 11/1988 | Toft et al. | 502/8 |
| 4,797,381 | 1/1989 | Bartek et al. | 502/202 |
| 4,801,568 | 1/1989 | Brazdil, Jr. et al. | 502/209 |
| 4,835,125 | 5/1989 | Glaeser et al. | 502/202 |
| 4,837,191 | 6/1989 | Glaeser et al. | 502/202 |
| 4,843,055 | 6/1989 | Glaeser et al. | 502/202 |
| 4,849,537 | 7/1989 | Ramachandran | 558/319 |
| 4,849,538 | 7/1989 | Ramachandran et al. | 558/319 |
| 4,866,024 | 9/1989 | Brazdil et al. | 502/209 |
| 4,870,201 | 9/1989 | Ramachandran et al. | 558/319 |
| 4,871,706 | 11/1989 | Brazdil et al. | 502/209 |
| 4,874,738 | 11/1989 | Brazdil et al. | 502/209 |
| 4,877,764 | 11/1989 | Glaeser et al. | 502/209 |
| 4,879,264 | 11/1989 | Toft et al. | 502/8 |
| 4,880,764 | 11/1989 | Imai | 502/326 |
| 5,177,048 | 1/1993 | Chen et al. | 502/212 |
| 5,212,137 | 5/1993 | Suresh et al. | 502/212 |

OTHER PUBLICATIONS

Young–Chul Kim et al., Selective Ammoxidation of Propane Involving Homogeneous and Heterogeneous Stepts over Multicomponent Metal Oxide Catalysts, Applied Catalysis, 70:189–196 (1991).

G. Centi et al., Functionalization of Alkanes by Heterogeneous Vapor–Phase Oxidation, Applied Catalysis, 33:343–359 (1987).

Robert Catani et al., Kinetics and Reaction Network in Propane Ammoxidation to Acrylonitrile on V–SB–A1 Based Mixed Oxides, Ind., Eng. Chem. Res. 1991 31, 107–119.

G. Centi et al., Synthesis of Acrylonitrile from Propane on V–SB–Based Mixed Oxides, New Developments in Selective Oxidation, Elsevier Science Pub.: Amsterdam 1990 515.

Applied Catalysis A: General 110 (1994) 173–184, "Selective ammoxidation of Propane over Ca–Bi–Mo Oxide Catalyst", Jong Seob Kim et al.

*Primary Examiner*—Anthony McFarlane
*Attorney, Agent, or Firm*—Ostrolenk, Faber, Gerb & Soffen

[57] ABSTRACT

The present invention relates to a novel multicomponent oxide catalyst, more specifically, a highly active and selective catalyst composition which plays a vital role to produce unsaturated nitrile compounds by reacting paraffinoid hydrocarbons with ammonia and oxygen. The formula of catalyst composition of the present invention is represented as $A_aB_bC_cD_dIn_e\ Ga_fBi_gMo_iO_x$, wherein:

A is alkali metal, alkali earth metal, silver or copper;
B is nickel, cobalt, iron, chromium, ruthenium, palladium or manganese;
C is zinc, cadmium, cerium, tin, phosphorus, antimony, lead, tellurium, germanium or aluminum;
D is titanium, zirconium, vanadium, niobium, tantalum, lanthanum, neodymium, gadolinium or tungsten; and, a, b, c, d, e, f, g and i is the mole of each component, wherein, a is 0 to 10; b is 0 to 5; c is 0 to 15; d is 0 to 14; e is 0 to 2; f is 0 to 7; g is 1 to 25; i is 12 to 40; and, $12 \leq a+b+c+d+e+f+g \leq 40$.

5 Claims, No Drawings

MULTICOMPONENT OXIDE CATALYST

FIELD OF THE INVENTION

The present invention relates to a novel multicomponent oxide catalyst, more specifically, a highly active and selective catalyst composition which plays a vital role to produce unsaturated nitrile compounds by reacting paraffinoid hydrocarbons with ammonia and oxygen.

BACKGROUND OF THE INVENTION

In general, acrylonitrile is prepared on industrial scale by an ammoxidation reaction of an unsaturated hydrocarbon, i.e., propylene. However, it has been reported that propane instead of propylene, can also be employed in the ammoxidation reaction more economically; and, therefore, the development of catalysts for the ammoxidation of propane, has been one of the most important tasks in the art.

On the other hand, prior art catalysts which function to produce acrylonitrile, mono- or binary component oxide metal catalysts, have not been employed in industrial process in a practical manner, due to their low activity and selectivity. In this connection, studies on the ammoxidation reaction of propane to acrylonitrile have been extensively carried out in Japan and U.S.A. in order to develop highly active and selective multicomponent oxide catalysts which are practically applied for producing acrylonitrile compounds.

Under the circumstance, a number of multicomponent oxide catalysts have been suggested as highly active and selective catalysts, which are prepared by the addition of alkyl halide such as bromoethane (0.2 mole %) to Bismuth-iron (Bi—Fe) oxide catalyst, Uranium-Antimony (U—Sb) oxide catalyst and Bismuth-Tellurium-Molybdenum (Bi—Te—Mo) oxide catalyst, respectively [see: U.S. Pat. Nos. 3,670,008; 3,816,506; and, 3,833,638]. However, special materials to prevent corrosion should be employed in reactors or plants because the halogen compound such as bromoethane gives rise to strong corrosiveness.

On the other hand, U.S. Pat. No. 4,609,502 teaches a process for preparing acrylonitrile by the ammoxidation, which employs propylene produced by dehydrogenation of propane. However, said dehydrogenation process of propane has caused undesirable economical problems in light of plant investment in comparison with the ammoxidation of propylene.

G. Centi et al. reported that introduction of aluminum oxide ($Al_2O_3$) to the Vanadium-Antimony (V—Sb) oxide catalyst, improved in terms of selectivity for acrylonitrile, grounded on the change of catalyst structure: however, said catalyst was not applied on industrial scale because of its limitation on selectivity and performance [see: G. Centi, R. K. Grasselli, E. Patane, F. Trifiro, in New Developments in Selective Oxidation, Elsevier Science Pub.: Amsterdam 1990, 515].

Under the circumstances, several catalysts have been proposed as effective catalysts under high level of propane in the reactants: for example, multicomponent catalyst which various metal components was added to Vanadium-Antimony (V—Sb), mixed oxide catalyst (U.S. Pat. No. 4,797,381), Bismuth-Cerium-Molybdenum (Bi—Ce—Mo) mixed oxide catalyst and Bismuth-Iron-Molybdenum (Bi—Fe—Mo) mixed oxide catalyst (U.S. Pat. No. 4,760,159); and, multicomponent catalysts produced by mixing the latter two catalysts (U.S. Pat. No. 4,877,764).

Some other literature also discloses that the multicomponent oxide catalyst known as effective for selective oxidation reaction, provides a good performance relatively, and selective conversion of propane to acrylonitrile depends on the kinds of metal elements of multicomponent oxide catalyst and the amount of each component. However, it was still undesirable to use said catalysts on industrial scale owing to their low activity and selectivity. Therefore, need has continued to exist for the development of a highly active and selective catalyst, which is practically employed in industrial process.

SUMMARY OF THE INVENTION

In accordance with the present invention, the present inventors developed a novel multicomponent oxide catalyst, which can be employed in the ammoxidation of propane to acrylonitrile in a highly active and selective manner.

A primary object of the present invention is, therefore, to provide a novel multicomponent oxide catalyst with high activity and selectivity.

Another object of the present invention is to provide a process for preparing acrylonitrile from propane by employing said catalyst.

DETAILED DESCRIPTION OF THE INVENTION

For the ammoxidation of propane to acrylonitrile, two steps should be involved in the reaction: first, conversion of propane to propylene which is a rate determining step; second, conversion of propylene to acrylonitrile. In this connection, the present inventors discovered that a multicomponent oxide catalyst, which is prepared by mixing metal components known as effective for selective oxidation reaction with alkali metal, alkaline earth metal and 8A-group transition metal components and so on, has excellent activity and selectivity in the process for preparing acrylonitrile from propane.

The formula of catalyst composition of the present invention is represented as $A_a B_b C_c D_d In_e Ga_f Bi_g Mo_i O_x$, wherein:

A is alkali metal, alkaline earth metal, silver or copper;

B is nickel, cobalt, iron, chromium, ruthenium, palladium or manganese;

C is zinc, cadmium, cerium, tin, phosphorus, antimony, lead, tellurium, germanium or aluminum;

D is titanium, zirconium, vanadium, niobium, tantalum, lanthanum, neodymium, gadolinium or tungsten; and, a, b, c, d, e, f, g and i is the mole of each component, wherein, a is 0 to 10; b is 0 to 5; c is 0 to 15; d is 0 to 14; e is 0 to 2; f is 0 to 7; g is 1 to 25; i is 12 to 40; and, $12 \leq a+b+c+d+e+f+g \leq 40$.

As a more preferred embodiment, the catalyst of the present invention, further comprises 5 to 99% (w/w) support materials such as $Al_2O_3$, $SiO_2$, $TiO_2$, MgO and SiC.

In accordance with the invention, acrylonitrile is prepare, d with a high selectivity under high level of propane in reactants, i.e., under the condition that molar ratio of propane/oxygen is 0.1 to 15, propane/ammonia is 0.5 to 10, and the other additives are not further involved. The present inventors also determined that the activities of various multicomponent metal oxide catalysts of the invention were increased at the following calcination conditions: temperature range of 320° C. to 650° C., preferably at 350° C. to 650° C., reaction time of 30 min to 10 hr and elevating temperature velocity of below 15° C./min. Therefore, the present invention further comprises the catalyst prepared by the calcination of said catalyst composition in the air or oxygen, at the temperature 320° C. to 650° C., and elevating temperature velocity of below 15° C./min.

On the other hand, the present inventors employed a series of physical methods such as coprecipitation, impregnation and mixing in the process for preparing said catalyst; and, employed starting materials such as ammoniums, carbonates, nitrates, acetates and oxide compounds, preferably water-soluble compounds; and halogen compounds are not employed in the catalyst composition.

Process for preparing multicomponent oxide catalyst of the invention were as following starting materials such as ammoniums and nitrates were dissolved in distilled water under heating and, the reactants were mixed slowly to obtain a precipitate and heated to evaporate water; and precalcinated in an air stream to produce multicomponent oxide catalyst of the invention. In this connection, the catalyst prepared by the addition of various activating agent to Ca—Ga—Bi—Mo mixed oxide is most preferable, in terms of conversion of propane and selectivity of acrylonitrile under high level of propane in reactants.

The present invention is further illustrated in the following examples, which should not be taken to limit the scope of the invention.

EXAMPLE 1

To the mixture of 150 ml distilled water and 10 ml nitric acid was added bismuth nitrate, lead nitrate, cobalt nitrate, silver nitrate, magnesium nitrate, nickel nitrate, cerium nitrate and gallium nitrate. The resulting mixture ('solution 1') was stirred under heating and maintained at 80° C. Then, ammonium molybdate was dissolved in 50 ml of distilled water and this solution ('solution 2') was added dropwise to the solution 1 with vigorous stirring to evaporate water; and, the resultant precipitate was obtained and dried at 120° C. for 24 hours in dry oven. Dried precipitate was precalcined at 320° C. in the air stream, and ground to the powders of 100 and 200 mesh and finally calcined at 520° C. for 6 hours in the air stream to provide Ag(1)Pb(1)Mg(1)Co(1)Ni(1)Ce(1)Ga(1)Bi(7)Mo(14) oxide catalyst composition.

EXAMPLE 2

Same catalyst composition was prepared by the process of Example 1, with the exception of precalcination at 710° C. for 6 hours.

EXAMPLE 3

To the mixture of 150 ml distilled water and 10 ml nitric acid was added indium nitrate, bismuth nitrate, lead nitrate, cobalt nitrate, silver nitrate, magnesium nitrate, nickel nitrate and cerium nitrate. The resulting mixture ('solution 1') was stirred under heating and maintained at 80° C. Then, ammonium molybdate was dissolved in 50 ml of distilled water and this solution ('solution 2') was added dropwise to the solution 1 with vigorous stirring to evaporate water; and, the resultant precipitate was obtained and dried at 120° C. for 24 hours in dry oven. Dried precipitate was precalcined at 320° C. in the air stream, and ground to the powders of 100 and 200 mesh and finally calcined at 520° C. for 6 hours in the air stream to provide Ag(1)Pb(1)Mg(1)Co(1)Ni(1)Ce(1)In(1)Bi(7)V(2)Mo(12) oxide catalyst composition.

EXAMPLE 4

Same catalyst composition of Example 1 was supported with $TiO_2$ as followings: $TiO_2$ was dissolved in 300 ml of distilled water; and, to the solution was added catalyst composition prepared by the Example 1 with a ratio of 1:1 (w/v) and dried for 5 hours in rotavapor. Dried catalyst was calcined under the temperature of 520° C. for 6 hours in an air stream.

EXAMPLE 5

Oxide catalyst composition of Mg(0.8)Bi(22.5)V(14)Mo(12) was prepared by the same process of Example 3.

EXAMPLE 6

Oxide catalyst composition of Zn(4)Ga(2)Bi(22.5)V(14)Mo(12) was prepared by the same process of Example 3.

EXAMPLE 7

Oxide catalyst composition of Co(0.3)Bi(22.5)V(14)Mo(12) was prepared by the same process of Example 3.

EXAMPLE 8

Oxide catalyst composition of Ca(0.5)Bi(22.5)Nb(14)Mo(12) was prepared by the same process of Example 1.

EXAMPLE 9

Oxide catalyst composition of Pb(0.3)Bi(22.5)V(14)Mo(12) was prepared by the same process of Example 3.

EXAMPLE 10

Oxide catalyst composition of Ag(1)Pb(1)Mg(1)Co(1)Ni(1)Ce(1)Bi(7)Mo(12) was prepared by the same process of Example 1.

EXAMPLE 11

Oxide catalyst composition of Ga(0.5)Bi(22.5)V(14)Mo(12) was prepared by the same process of Example 3.

EXAMPLE 12

Oxide catalyst composition of Mg(3)Bi(15)Ga(6)Mo(12) was prepared by the same process of Example 1.

EXAMPLE 13

Oxide catalyst composition of Ni(3)Bi(15)Ga(6)Mo(12) was prepared by the same process of Example 1.

EXAMPLE 14

Oxide catalyst composition of Ga(0.3)Bi(24)Ti(12)Mo(12) was prepared by the same process of Example 1.

EXAMPLE 15

Oxide catalyst composition of Ca(6)Bi(6)Mo(12) was prepared by the same process of Example 1.

EXAMPLE 16

Oxide catalyst composition of Ag(1)Ce(1)Ga(2)Ca(6)Bi(3)Mo(12) was prepared by the same process of Example 1.

EXAMPLE 17

Oxide catalyst composition of Ca(0.5)Ga(0.1)Bi(22.4)V(14)Mo(12) was prepared by the same process of Example 3.

The ammoxidation process of propane employing catalysts prepared in Examples 1 to 17, was carried out at atmospheric pressure by means of a continuous flow reactor system which is equipped to guarantee proper dead volume after filling of catalysts and to carried out gas phase radical reaction of reactants. The reactants, i.e. propane, oxygen and ammonia were filled to the reactor system which is already filled with catalysts by a mass flow controller, which controls feed velocity and concentration of components. A quartz tube (i.d.=20 mm) was employed as the reactor. The conversion of the reactant, the selectivity of the product and contact rate of catalyst were defined as followings:

The conversion of the propane (%)=(1–-mole of propane remained/mole of propane in feed)×100

The selectivity of the product A (%)=(mole of A product×the number of C in product)/(mole of propane consumed×3)×100

The contact rate of catalyst =the volume of catalyst (cc)/feed rate of reactant (cc/sec)

Results of ammoxidation employing the catalysts prepared by each Example are disclosed in Table 1.

TABLE 1

Results of ammoxidation employing the catalysts of the invention

| Catalyst (Examples) | Reaction temperature (°C.) | Contact time (sec) | Feed composition $C_3H_8/O_2/NH_3$ (%) | Conversion of propane (%) | Selectivity propylene | AN* |
|---|---|---|---|---|---|---|
| 1 | 510 | 1.0 | 63/25/12 | 17.2 | 1.8 | 65.1 |
|   | 490 | 1.0 | 63/25/15 | 10.5 | 2.1 | 65.5 |
|   | 510 | 1.0 | 44/41/15 | 18.8 | 7.4 | 63.2 |
|   | 545 | 1.0 | 8/80/12 | 29.6 | 0.0 | 60.2 |
| 2 | 490 | 1.0 | 63/25/12 | 20.0 | 64.0 | 7.5 |
| 3 | 495 | 1.0 | 63/25/12 | 15.1 | 3.0 | 63.0 |
|   | 485 | 1.0 | 44/41/15 | 26.2 | 8.5 | 55.9 |
| 4 | 500 | 1.0 | 63/25/12 | 16.8 | 19.5 | 50.0 |
| 5 | 470 | 1.0 | 73/18/9 | 12.1 | 6.9 | 59.4 |
| 6 | 470 | 1.0 | 73/18/9 | 5.7 | 11.7 | 52.8 |
| 7 | 485 | 1.0 | 73/18/9 | 10.1 | 9.3 | 60.1 |
| 8 | 500 | 1.0 | 73/18/9 | 11.5 | 4.7 | 55.8 |
| 9 | 480 | 1.0 | 73/18/9 | 11.6 | 14.1 | 56.8 |
| 10 | 500 | 1.0 | 63/25/12 | 18.0 | 6.1 | 60.1 |
|   | 510 | 1.0 | 44/41/15 | 30.5 | 2.6 | 55.3 |
| 11 | 490 | 1.0 | 63/25/12 | 16.1 | 17.6 | 52,4 |
| 12 | 500 | 1.0 | 63/15/12 | 15.0 | 11.0 | 64.5 |
|   | 530 | 1.0 | 44/41/15 | 29.0 | 17.1 | 51.6 |
| 13 | 510 | 1.0 | 63/25/12 | 15.4 | 11.4 | 62.9 |
| 14 | 515 | 1.0 | 63/25/12 | 21.1 | 4.6 | 55.1 |
|   |   |   | 44/41/15 | 37.0 | 3.4 | 51.0 |
| 15 | 505 | 1.0 | 63/25/12 | 16.9 | 13.9 | 56.3 |
|   | 495 | 1.0 | 73/18/9 | 12.6 | 18.2 | 53.7 |
|   | 520 | 1.0 | 44/41/15 | 32.5 | 11.7 | 50.3 |
| 16 | 480 | 1.0 | 63/25/12 | 15.8 | 10.6 | 62.1 |
| 17 | 490 | 1.0 | 63/25/12 | 14.8 | 6.4 | 63.7 |

*AN: acrylonitrile

What is claimed is:

1. A multicomponent oxide catalyst composition for preparing acrylonitrile from propane by ammoxidation which is AgPbMgCoNiCeGaBi$_7$Mo$_{14}$ oxide.

2. A multicomponent oxide catalyst composition for preparing acrylonitrile from propane by ammoxidation which is AgPbMgCoNiCeBi$_7$Mo$_{12}$ oxide.

3. A multicomponent oxide catalyst composition for preparing acrylonitrile from propane by ammoxidation which is Mg$_3$Bi$_{15}$Ga$_6$Mo$_{12}$ oxide.

4. A multicomponent oxide catalyst composition for preparing acrylonitrile from propane by ammoxidation which is Ga$_{0.3}$Bi$_{24}$TiMo$_{12}$ oxide.

5. A multicomponent oxide catalyst composition for preparing acrylonitrile from propane by ammoxidation which is Ca$_6$Bi$_6$Mo$_{12}$ oxide.

* * * * *

UNITED STATES PATENT AND TRADEMARK OFFICE
CERTIFICATE OF CORRECTION

PATENT NO.   : 5,470,815
DATED        : November 28, 1995
INVENTOR(S)  : Jong-Seob Kim, et. al.

It is certified that error appears in the above-indentified patent and that said Letters Patent is hereby corrected as shown below:

Title page, item [73], "Istitue" should read --Institute--.

Signed and Sealed this

Twenty-fourth Day of September, 1996

Attest:

BRUCE LEHMAN

*Attesting Officer*          *Commissioner of Patents and Trademarks*